United States Patent [19]

Yeo et al.

[11] Patent Number: 5,695,855
[45] Date of Patent: Dec. 9, 1997

[54] DURABLE ADHESIVE-BASED INK-PRINTED POLYOLEFIN NONWOVENS

[75] Inventors: Richard Swee-chye Yeo, Dunwoody, Ga.; Brigitte Kay Weigert, Oshkosh, Wis.; David George Crowther, High Point, N.C.

[73] Assignee: Kimberly-Clark Worldwide, Inc., Neenah, Wis.

[21] Appl. No.: 761,478

[22] Filed: Dec. 6, 1996

Related U.S. Application Data

[63] Continuation of Ser. No. 587,770, Dec. 21, 1995, abandoned, which is a continuation of Ser. No. 224,403, Apr. 7, 1994, abandoned, which is a continuation of Ser. No. 998,083, Dec. 29, 1992, abandoned.

[51] Int. Cl.$^6$ .............................. A61L 15/20; A61L 15/42
[52] U.S. Cl. ............... 428/196; 428/207; 428/355 EN; 442/149; 442/333
[58] Field of Search ........................... 428/195, 196, 428/197, 200, 207, 355 EN; 442/149, 330, 333

[56] References Cited

U.S. PATENT DOCUMENTS

| | | | |
|---|---|---|---|
| 3,732,139 | 5/1973 | Fechillas | 428/288 |
| 3,867,171 | 2/1975 | Ellsworth | 428/195 |
| 3,873,486 | 3/1975 | Drelich | 428/288 X |
| 3,973,067 | 8/1976 | Newman | 428/195 |
| 4,041,203 | 8/1977 | Brock et al. | 428/340 X |
| 4,235,657 | 11/1980 | Greenman et al. | 428/200 X |
| 4,423,676 | 1/1984 | Neel | 101/211 |
| 4,530,874 | 7/1985 | Hendrix et al. | 428/266 |
| 4,574,732 | 3/1986 | Verwey et al. | 118/642 |
| 4,610,920 | 9/1986 | Mudge et al. | 428/290 X |
| 4,623,575 | 11/1986 | Brooks et al. | 428/288 X |
| 4,646,362 | 3/1987 | Heran et al. | 2/400 |
| 4,702,957 | 10/1987 | Mudge | 428/290 X |
| 4,713,068 | 12/1987 | Wang et al. | 604/366 |
| 4,713,069 | 12/1987 | Wang et al. | 604/378 |
| 4,758,239 | 7/1988 | Yeo et al. | 604/366 |
| 4,766,840 | 8/1988 | Beckley et al. | 118/46 |
| 4,796,556 | 1/1989 | Bird | 118/46 |
| 4,818,600 | 4/1989 | Braun et al. | 428/290 |
| 4,828,556 | 5/1989 | Braun et al. | 604/365 |
| 4,841,903 | 6/1989 | Bird | 118/46 |
| 4,844,952 | 7/1989 | Korenkiewicz et al. | 427/258 |
| 4,939,992 | 7/1990 | Bird | 101/183 |
| 4,940,464 | 7/1990 | Van Gompel et al. | 604/396 |
| 5,163,247 | 11/1992 | Weber et al. | 47/9 |
| 5,187,226 | 2/1993 | Kamachi et al. | 525/56 |

FOREIGN PATENT DOCUMENTS

| | | |
|---|---|---|
| 0 442 673 | 1/1984 | European Pat. Off. . |
| 0120579 | 10/1984 | European Pat. Off. ......... D04H 1/66 |
| 3-234704 | 10/1991 | Japan . |

OTHER PUBLICATIONS

A. Uyoshihalu, "Nonwoven Fabrics For Commodities" *Journal of the Textile mach. Society of Japan*, Osaka, Japan, Mar. 1992, pp. 166–170.

K. Lai, "Chemicals For Colour Paste", *Practical Techniques On Colour Paste For Textile Printing*, Tainan, Taiwan, Apr. 1990, pp. 74–89.

"Thickening Agents", *Handbook of Textile*, Publishing Committee of Handbook of Textile, Taipei, Taiwan, 1973, pp. 899–909.

Patent Abstracts of Japan. vol. 012, No. 467 (C–550) 7 Dec. 1988 & JP–A–63 189 485 (Sekisui Chem. Co. Ltd.) 5 Aug. 1988, Abstract.

AATCC Test Method 116–1983.
AATCC Test Method 8–1972.
AATCC Test Method 153–1985.

*Primary Examiner*—Daniel Zirker
*Attorney, Agent, or Firm*—Patrick C. Wilson

[57] ABSTRACT

Disclosed herein is a durable adhesive-based ink-printed polyolefin nonwoven which is suitable for a number of uses the most basic of which is where a printed nonwoven is needed and that nonwoven will possibly be subjected to an amount of abrasion which would prematurely remove the ink from the surface of the nonwoven web. The two main components of the present invention are an adhesive-based ink and a polyolefin-based substrate onto which the adhesive-based ink is applied. The resultant composite must have a crock value of 4 or greater.

5 Claims, No Drawings

DURABLE ADHESIVE-BASED INK-PRINTED POLYOLEFIN NONWOVENS

This application is a continuation of application Ser. No. 08/587,770, abandonded, entitled "DURABLE ADHESIVE-BASED INK-PRINTED POLYOLEFIN NONWOVENS" and filed in the U.S. Patent and Trademark Office on Dec. 21, 1995; which is a continuation of application Ser. No., now abandonded, 08/224,403 entitled "DURABLE ADHESIVE-BASED INK-PRINTED POLYOLEFIN NONWOVENS" and filed in the U.S. Patent and Trademark Office on Apr. 7, 1994; which is a continuation of application Ser. No. 07/998,083 abandonded, entitled "DURABLE ADHESIVE-BASED INK-PRINTED POLYOLEFIN NONWOVENS" and filed in the U.S. Patent and Trademark Office on Dec. 29, 1992. The entirety of this application is hereby incorporated by reference.

TECHNICAL FIELD OF THE INVENTION

The present invention is directed to a printed nonwoven. More specifically, the printed nonwoven is made from a polyolefin substrate such as a polyolefin fibrous web which is printed with an adhesive ink to yield a printed nonwoven wherein the adhesion of the ink to the web is very strong.

BACKGROUND OF THE INVENTION

The printing of substrates such as woven and nonwoven fabrics and films is well known. The printing of fabrics with inks and dyes is a common and widely used method of imparting patterns and colors to a base fabric. Generally speaking, color printing on cellulosic substrates such as cotton is relatively easy to do. Printing on polar polymers such as nylon and polyester is also possible but is more difficult than the same type of printing on cellulosic materials. More difficult than either of these substrates is the printing of non-polar polymers such as polyolefins. This is particularly true of fibrous polyolefin structures such as nonwovens because the inks and dyes have limited adhesion to these non-polar materials. Ink print adhesion to polyolefin nonwovens can be somewhat improved through the use of corona discharge treatment on the nonwoven, however, this requires an additional step in the printing process along with higher energy costs. In addition, if the corona discharge treatment is not carefully monitored, there is the possibility that the treatment will burn the nonwoven substrate thereby increasing production costs due to the waste of damaged material.

In ink printing fabrics such as nonwovens it is desirable to have the ink strongly adhere to the nonwoven substrate. The degree of durability or adhesion of the ink to the substrate can be reflected by a parameter called crockfastness. Crockfastness is measured on a scale from 0 to 5, with 5 being the highest, of the resistance of a material to the transfer of its color to another material. Heretofore, it has been possible to create printed nonwovens with crockfastness values approaching 4. However, to achieve values above 4 in the past it has been necessary to use nonconventional inks such as synthetic-paper inks, ultraviolet (UV)-curing inks and electron-beam-curing inks, all of which are expensive. It has been found that the use of synthetic-paper inks greatly impairs printing workability in that synthetic paper inks require longer drying times thus making the printing process slower and more complex. To utilize UV-curing ink or electron-beam(EB)-curing ink, expensive UV and EB generators must be employed for curing the inks which makes it difficult to carry out the printing process at a low cost. Another method for improving the crockfastness of printing on nonwovens is to utilize an underlacquer and/or overlacquer. The underlacquer adheres to the nonwoven and creates a surface to which the ink can better adhere while the overlacquer creates a protective coating for the ink. Here again, however, the use of such protective coatings is not as desirable as it creates additional processing steps and also increases the cost of printing.

It is therefore an object of the present invention to provide both a process and a material which include an ink-printed polyolefin nonwoven with good crockfastness. This is particularly useful in the area of personal care products such as diapers, training pants, incontinence products, feminine products and the like. Many up-to-date personal care products, diapers and training pants being an example, include printed designs on the outside of the products to improve their appearance. A problem with printing such products is a result of the use and abrasion that they encounter. The crawling action of babies and small children subjects the exterior portion of the diaper and training pant to a high degree of abrasion. Such abrasion will quickly remove any printing which is not durably adhered to the outer surface of the product. Many of these products employ polyolefins in the manufacture of the component materials. There is therefore a need for an ink-printed polyolefin nonwoven which is abrasion resistant so as to reduce premature wear of the printed design on the nonwoven fabric and the possible transfer of the ink to other surfaces.

It is another object of the present invention to provide an ink-printed polyolefin nonwoven which can be adapted for a wide variety of other uses including garments, workwear, cleanroom clothing, hospital gowns and related supplies. In hospital and cleanroom applications it is important that any clothing that is worn have a low lint characteristic. Conversely, much of such clothing is very mundane in nature and research has indicated that people prefer wearing more colorful garments. Because such materials are made from nonwovens, it is not possible to create single or multicolor designs without printing directly onto the surface of the nonwoven. When such printing is performed, it is important that the ink remain durably affixed to the nonwoven material and not flake off as the portions of the ink which flake off can result in possible contamination of the patient. As a result, it is an object of the present invention to provide an ink-printed nonwoven which can be used in such applications.

These and other objects of the present invention will become more apparent upon a further review of the following specification and claims.

SUMMARY OF THE INVENTION

The present invention is directed to a durable, adhesive-based ink-printed nonwoven and a process for forming the same. The process first involves positioning a polyolefin nonwoven web such that it is capable of receiving a printing pattern on at least one surface of the nonwoven web. Next an adhesive-based ink is applied to the surface of the nonwoven web and then allowed to dry so as to yield an adhesive-based ink-printed nonwoven web with a crock value of 4 or greater. If ink printing equipment is being used to apply the adhesive-based ink to the nonwoven, then the process may further include the step of first transferring the adhesive-based ink to a transfer surface on the ink printing equipment and then transferring the adhesive-based ink to the nonwoven substrate. Furthermore, to speed up the process, heat may be applied to the printed nonwoven to hasten drying. The adhesive-based ink includes a binder selected from the group consisting of water-based, solvent-based and hot-melt adhesives with the adhesive-based ink having a viscosity of between about 50 and 10,000 centipoise during application. The adhesive-based ink further includes a pigment with a binder to pigment ratio of between about 10:1 and 1:1 on a dry weight basis of the total solids content in the adhesive-based ink. Examples of suitable binder materials include polyvinyl alcohol, ethylene vinyl acetate, and water-based acrylic copolymers. To aid in the application of the adhesive-based ink to the nonwoven substrate, the adhesive-based ink may further include a tackifying agent such as polyterpene or a rosin ester. When the binder is a water-based material a surfactant may also be used. In addition, both foaming agents and plasticizers may be used in the adhesive-based ink formulation.

The durable, adhesive-based ink-printed nonwoven web of the present invention is useful in a number of applications including medical fabrics and personal care absorbent articles such as diapers, training pants, incontinence garments, feminine hygiene products and bandages.

DETAILED DESCRIPTION OF THE INVENTION

The present invention is directed to the combination of an adhesive-based ink and a polyolefin-based nonwoven web with the resultant ink-printed nonwoven having good crockfastness which is an indication of abrasion resistance and good colorfastness.

The ink-printed polyolefin-based nonwoven web of the present invention is suitable for a number of uses the most basic of which is where a printed nonwoven is needed and that nonwoven will possibly be subjected to an amount of abrasion which would prematurely remove the ink from the surface of the nonwoven web. There are many applications where nonwoven webs are utilized and where it is desirable to have some type of printing, indicia, instructions, or general patterns printed directly onto the nonwoven web. Such printing can be single color or multiple color depending upon the aesthetic needs of the material. Personal care products such as diapers, feminine pads, adult incontinence garments and training pants all typically have an outer cover which may include an external layer of nonwoven material. With many of these products, it is desirable to have one or more designs in one or more colors printed on the product such that they are visible to the consumer—training pants being an example. With training pants such as PULL-UPS® brand training pants manufactured by the assignee of record, Kimberly-Clark Corporation, it is desirable to make the product as attractive and fun as possible to wear in order to train the child to progress from diapers to underwear. One means to make this product more appealing is to print in bright colors a number of designs on the exterior cover of the training pant. Heretofore, it is not been possible to directly print colored inks onto the exterior surface of the training pant without costly under and/or over lacquers to protect the ink from abrasion. As a result, it has been necessary to print these colored designs on the underlying film layer and then superimpose the nonwoven outer layer over top of the printed film layer such that the colored designs can be viewed, albeit somewhat diffusely, through the nonwoven layer. The present invention alleviates the need for such printing techniques due to the combination of an adhesive-based ink and a polyolefin-based nonwoven which together yield a high abrasion resistance as measured by a crockfastness value of at least four or greater.

The same type of material also has potential applicability in the medical field in conjunction with disposable goods used in hospitals. Such disposable goods include surgical drapes, patient and employee gowns, shoe covers, headwear, masks, covers and bedding. Here again it has been found that hospital staff who routinely wear such disposable items grow tired of the plain look of the products. As a result, it has been found that when such disposable goods are printed with colored patterns and figures, the products become more desirable to wear. It should be noted, however, that when such products are used during surgical procedures, it is important that as little of the material as possible, including the ink, separate from the product as anything that is released in the operating room can become a possible contaminant to a surgical site or open wound on a patient. Consequently, if such products are to be printed with figures and patterns, the inks used to print these products must be durable so as to reduce the possibility of contamination. Many of these products also include identification codes and instructions printed directly on the product, surgical drapes being but one example. As a result, these products must also utilize ink-printed materials which have good abrasion resistance.

The foregoing examples are but a few of the possible uses for the material of the present invention. As a result, such uses should be considered as illustrative only and therefore not limiting as to the scope of the application of the present invention.

The two main components of the present invention are the adhesive-based ink and the polyolefin-based substrate onto which the ink is applied. Polyolefin-based substrates include, but are not limited to, woven materials, nonwoven materials, knits and films which employ polyolefin-based polymers. Examples of commonly employed polyolefins are polypropylene and polyethylene including low density, high density and linear low density polyethylene. It should be appreciated however that the present invention is not limited to these two types of polyolefins, but instead, is intended to embrace all types of polyolefins and polyolefin blends. In woven material applications these polyolefin-based polymers can be made into continuous fibers which are in turn woven into a fabric. In nonwoven applications, the fibers may be long, generally continuous fibers such as spunbond and meltblown fibers or they may be shorter staple length fibers such as are commonly used in carded webs. Lastly, such polyolefin-based polymers may be extruded, cast or blown into films for subsequent use according to the present invention.

A number of nonwovens are suitable for use with the present invention including spunbond and meltblown webs as well as bonded carded webs using staple fibers. In addition, air laid, wet laid, as well as solution spun fiber webs and other webs and web forming processes are also considered to be within the scope of the present invention provided they can accommodate the generation of polyolefin-based or polyolefin-containing fibrous webs.

The fibers used for the substrate may be "straight" fibers in that they have the same general polymer composition throughout or they may be multipolymer or multicomponent fibers such as bicomponent fibers where at least one component is a polyolefin such as a polyethylene sheath and a polypropylene core fiber or a polyethylene sheath and a polyester core fiber. In addition to sheath/core fiber configurations, side-by-side, sea-in-islands and eccentric fiber configurations are other examples of suitable fiber cross-sections. Furthermore, fibers with non-circular cross-sections such as "Y" and "X" shapes may be used.

The fibers and/or webs may have other components and/or treatments. For example, adhesives, waxes, flow modifiers, processing aids and other additives may be used during the formation of the fibers and webs. In addition, pigments may be added to the fibers to change their color and other additives may be incorporated into the polymer compositions to make the fibers and/or webs elastic. Lastly, blends of fibers including polyolefin and non-polyolefin based fibers as well straight and bicomponent fibers may be combined to form nonwoven webs suitable for use with the present invention.

The polyolefin-based substrate material can be used by itself or in a multilayer configuration such as a laminate of one or more film and/or woven and/or nonwoven layers. Examples of such multilayer configurations include film/nonwoven laminates or nonwoven/nonwoven laminates such as a spunbond/meltblown/spunbond three layer laminate. By using such multilayer configurations, a variety of properties can be imparted to the laminate including breathability and/or liquid imperviousness.

When forming a nonwoven as the polyolefin-based substrate for the present invention, the fiber size and basis weight of the material can be varied according to the particular end use. In personal care product and medical fabric usage, typical fiber sizes will range from between about 0.1 to about 10 denier and basis weights will range from between about 0.3 and about 3 ounces per square yard. For other applications both the fiber size and the basis weight can be adjusted.

The other main component of the present invention is the ink for printing the polyolefin-based substrate. To achieve sufficient abrasion resistance and durability, testing has indicated that the ink, once applied to the polyolefin-based substrate, should have a crockfastness value of 4 or greater. Colorfastness is the resistance of a material to change in any of its color characteristics, to the transfer of its color to adjacent materials, or both as a result of the exposure of the material to any external conditions. Crocking is a transfer of colorant from the surface of a colored fabric to an adjacent area of the same fabric or to another surface principally by rubbing action. Testing for crockfastness is a method for determining whether or not a color may be transferred from the surface of the printed material to other surfaces by rubbing. As a result, crockfastness is a means for gaging the abrasion resistance of an ink once it has been printed onto a polyolefin-based substrate. This test is set forth in much greater detail below but suffice it to say that testing has shown that solvent-based inks when applied to polyolefin-based substrates such as a nonwoven web only exhibit crock ratings in the range of 1.5 to 3 and such solvent-based inks when covered with a clear overlacquer only increased their crock ratings to a range of 2.5 to 3.5. In contrast, the adhesive-based inks of the present invention can and do yield crock ratings in excess of 4 on a scale of 1 to 5. Thus, a necessary requirement of the present invention is that the adhesive-based inks when applied to a polyolefin-based substrate have a crock value or crockfastness of 4 or greater.

To this end, the adhesive-based inks of the present invention employ as primary constituents a binder and a pigment or dye. As will be explained in further detail below, other additives may be employed in the formulation of the adhesive-based inks used in conjunction with the present invention. Polyvinyl alcohol and ethylene vinyl acetate have been found to be particularly suitable as a base or binder for the inks of the present invention. It is also been found that the adhesive or binder in the adhesive-based inks can be water-based, solvent-based or hot-melt with water-based inks working the best from the combined standpoint of applicability to the substrate and resultant adhesion. The glass transition temperature ($T_g$) of these water-based polymer binders range from approximately −60° to 180° F. with a more desirable range being between about 20° and about 80° F. Such film-forming polymer binders produce flexible printed areas when dried or cured at relatively low drying temperatures which typically range between about 150° and 300° F. The solids level of these binder polymers (PVOH and EVA) in the adhesive-based inks is between approximately 5 and 60% by weight on a dry weight basis of the total solids in the adhesive-based ink.

Coloration can be imparted to these binders by the use on inert, pigments and dyes, collectively referred to as pigments for purposes of the claims, which can be added in levels of approximately 0.25 to 50% on a dry weight basis. Typically on a dry weight basis the solids level including all solids, not just the binder and pigment, will be 40% or greater for ethylene vinyl acetate and 8% or greater for polyvinyl alcohol. Other water-based adhesive ink binders include polyvinyl acetate, ethylene acrylic, vinyl acrylic, styrene acrylic, polyvinylidene chloride, starch, chemically modified starch, dextrin, and other latice and water-soluble polymers having film forming properties.

Suitable solvent-based binders for the adhesive-based inks of the present invention include natural rubber and other elastomers, acrylics, polyurethanes, polyamides, phenoxies, and poly(vinyl acetal)s. A related composition is vinyl resin dispersed in a plasticizer to form a plastisol. Before heating, the physical form of the plastisol actually resembles a dispersion. Upon heating the plastisol forms a solution of sufficiently high viscosity at room temperature such that the cured adhesive has excellent shear resistance. Several of these solvent-based binders are commercially available. National Starch and Chemical Company of Bridgewater, N.J. sells a neoprene rubber based adhesive using toluene, hexane, acetone and isopropanol as solvents under the trademark Spraymaster® 388.

Suitable hot-melt, adhesive binders for use in conjunction with the adhesive-based ink of the present invention include the more popular hot-melt adhesives based on polyethylene, other polyolefins or mixtures of the same, ethylene-vinyl acetate copolymers, polyamides, polyesters, and block copolymer rubbers. Typical additives used to modify the flow characteristics and other properties of these hot-melt adhesives include waxes, oils, terpene resins, rosin derivatives, phenolic resins (qv), and coumarone-indene resins. Hot-melt, adhesive binders are commercially supplied by many adhesive companies. Instant-Lok®, ethylene vinyl acetate-based adhesive is one example which is supplied by National Starch and Chemical Company of Bridgewater, N.J. Such hot-melt adhesives by their very nature will have a 100% solids content. These hot-melt, adhesive-based inks will typically melt and flow at temperatures ranging from between about 140° and about 300° F. For example, Instant-Lok® 34-4977 EVA-based adhesive has a softening temperature of 180° F. Its melt viscosity is 940, 590, 390 and 270 centipoise at temperatures of 250°, 275°, 300° and 325° F., respectively.

Due to the nature of these specific hot-melt adhesive-based inks, their application to nonwovens is generally restricted to rotogravure and screen printing types of ink applicating equipment. Furthermore, in selecting a hot-melt, adhesive-based ink for use in conjunction with the present invention, the choice of ink should involve a material which has an printing temperature which is below the melting temperature of the polymers used in the polyolefin-based substrate so that the hot-melt, adhesive-based ink does not damage the polyolefin-based substrate unless specifically desired. This is particularly true at low line speeds. At high line speeds it is possible to print at temperatures above the melting points of the polyolefins being used for the substrate due to the increased line speed.

Dyes and inorganic and organic pigments (collectively "pigments") are the common colorants used in conjunction with the present invention. The most common dyes include azo dyes (e.g. Solvent Yellow 14, Disperse Yellow 23, Metanil Yellow), anthraquinone dyes (Solvent Red 111, Disperse Violet 1, Solvent Blue 56 and Solvent Green 3), xanthene dyes (Solvent Green 4, Acid Red 52, Basic Red 1, and Solvent Orange 63), azine dyes (jet black) and the like.

Inorganic pigments include titanium dioxide (white), carbon black (black), iron oxides (red, yellow, brown), chromium oxide (green), ferric ammonium ferrocyanide (blue) and the like.

Major organic pigments include diarylide yellow AAOA (Pigment yellow 12), diarylide yellow AAOT (Pigment yellow 14), phthalocyanine blue (Pigment blue 15), lithol red (Pigment red 49:1) and Red lake C (Pigment red 53:1).

Most of these dyes and pigments are commercially supplied as color concentrates. For example, a blue pigment concentrate used with the present invention was copper phthalocyanine MONOLITE® blue BXE-HD from ICI Americas, Inc. of Wilmington, Del.

It appears as though the selection of the type of pigment or dye for use with the present invention is not crucial. However, there are some considerations in the selection. First, the pigment or dye should be inert and not react with the binder, additives or solvents present in the formulation. Second, the pigment or dye should be wetted out by the binder solution. It should disperse well and form a stable dispersion in the binder solution. Third, the pigment or dye should not pose any health problems or cause irritation to human skin. A binder to pigment ratio of between about 10:1 and 1:1 is suitable. This ratio is dependent on the color, shade and amount of ink being printed on the webs.

With the water-based, solvent-based, and hot-melt-based, adhesive inks, there is also the ability to incorporate other additives. For example, plasticizers, extenders, thickening agents, defoaming agents, wetting agents or surfactants, waxes and antioxidants may be utilized in conjunction with the adhesive-based inks of the present invention.

For most applications, the second most important ingredient in the adhesive-based ink is the plasticizer. Plasticizers are used to preserve the adhesive bond. Materials which are humectant and which act to preserve the adhesive film pliability by keeping the adhesive interface "moist" are suitable plasticizers. They have the ability to absorb atmospheric humidity and to retain it on a more-or-less permanent basis. The most common plasticizers are given in McCutcheon's Functional Materials (1991), pgs. 209–216. Typical of such materials are glycerine, sorbitol, ethylene glycol, and propylene glycol. On the other hand, compounds can act as plasticizers if they either enter into the molecular structure of the adhesive base or so effect the adhesive polymer so as to provide lasting film flexibility. Examples of such compounds include dialkyl phthalate, diaryl phthalate, alkyl aryl phthalate, dicyclohexyl phthalate, dibutoxyethyl phthalate, tirphenyl phosphate, tricresyl phosphate, cresyl diphenyl phosphate, alkyl diaryl phosphate, ethyl phthalyl ethyl glycolate, alkyl phthalyl ethyl glycolate, dialkyl adipate, alkyl stearate, alkyl lactate and fatty acid esters.

The vast majority of adhesive compounds and thus adhesive-based inks require some degree of "extension" or "loading" due to economic and functional considerations. In some cases, extension is desirable in the application process from the standpoint of controlling adhesive tack and flow. Typical extenders include bentonites, carbon black, carboxymethyl cellulose, clays, colodial silicas, diatomaceous earth, hydrated alumina, sodium alginate, starch and zinc oxide.

Thickeners are added to adhesive formulations to modify the adhesive viscosity and to provide for variations in applicator equipment or the substrates themselves. Basically, a thickener component is a gum or a resin material which possesses high intrinsic viscosity and which can be added to the adhesive formula in relatively small amounts. The most common thickeners are given in McCutcheon's Functional Materials (1991), pgs. 256–274. Examples of such thickeners include salts of alginates, stearates, and polyacrylates, starches, polyvinyl alcohols, bentonites, alkanolamide, carboxymethyl cellulose, hydroxyethyl cellulose, methyl cellulose, locust bean gum, guar gum, Xanthan gum, polystyrene sulfonic acid, polyalkyl sulfonic acid, sodium polyvinylates and polyvinylpyrrolidone.

The vast majority of adhesives are applied via machine applications. So are the adhesive-based inks of the present invention. In most cases, any repeated movement of the adhesive in an open atmosphere is likely to result in the entrainment of air bubbles. The entrained air alters the intrinsic viscosity of the adhesive and results in a variation in adhesive film thickness. It also can produce a discontinuous adhesive film which weakens the interface bond. Defoamers are used to reduce, or eliminate, the possibility of air entrainment during machine application of the adhesive. The most common defoamers are given in McCutcheon's Functional Materials (1991), pgs. 89–112. Typical defoamers include aluminum stearate, amyl alcohol, caprillic alcohol, capryl alcohol, castor oil, corn oil, dairy cream, decyl alcohol, diethylene glycol monolaurate, glyceryl monostearate, mineral oil, pine oil, polyalkyl glycol, silicone oils, stearic acid, sulfonic acid salts, tributyl citrate, tributyl phosphate and Turkey red oil. Also, there is a broad class of defoamer mixes which are available commercially. The more prominent mixes include Colloid from Rhone-Poulenc Corp. of Marietta, Ga.; Antifoam DB and 488 from Reilly-Whiteman, Inc. of Conshohocken, Pa.; Antifoam Base 263, Antifoam-G, and Antifoam-Q-41 from Soluol Chemical Co., Inc. of West Warwick, R.I.; Dow Corning Antifoam from Dow Corning Corp. of Midland, Mich.; Harcros Antifoam from Harcros Chemicals, Inc. of Kansas City, Mo.; Nopco and Foamaster from Henkel Corp. of Ambler, Pa.; AF from General Electric Co. of Waterford, N.Y.; Bubble Breaker® from Witco Corp. of Fort Worth, Tex. and Foam Blast from Ross Chem., Inc. of Fountain Inn, S.C.

The purpose of a wetting agent is to enhance the wetting of the adhered substrates by the adhesive-based inks in order to obtain a lasting adhesion. There are well over 100 proprietary or basic chemicals which have surfactant characteristics and which can be used as wetting agents. The most common surfactants are given in McCutcheon's Emulsifiers and Detergents (1991), pgs. 1–213. Listed below are some of the principal trademarked brands of materials which are used in the adhesive industry: Aerosol from American Cyanamid Co. of Wayne, N.J.; Duponol from E. I. dupont de Nemours of Wilmington, Del.; Emcol® from Wilco Corp. of Fort Worth, Tex.; Lubrizol from The Lubrizol Corp. of Wickliffe, Ohio; Nekal from Rhone-Poulenc Inc. of Cranberry, N.J.; Nonionic from Hodag Chemical Corp. of Skokie, Ill.; Nopcosulf from Henkel Corp. of Ambler, Pa.; Pluronic® from BASF Corp. of Parsippany, N.J.; Surfynol from Air Products & Chemicals, Inc. of Allentown, Pa.;

Tergitol® and Triton® from Union Carbide Chemical & Plastics Co. of Danbury, Conn. and Tween from ICI Americas Inc. of Wilmington, Del.

Preservatives are used to extend the shelf life of adhesives. The most common preservatives are given in McCutcheon's Functional Materials (1991), pgs. 216–218. Typical preservatives include benzoic acid, sorbic acid and their salts, chlorinated phenols, hydroxy benzoid esters, dihydroxybenzoic esters, alkyl paraben, phenols, salicylanilide, sodium propinates, and oxazoline blend.

In order to obtain wet tack, the adhesive compounder frequently manipulates the formula through the addition of a "tackifier". The tackifier itself often possesses good specific adhesive properties and thus reinforces the ability of the adhesive to adhere to difficult substrates. Tackifiers are primarily employed in aqueous adhesive systems and in particular in the compounding of natural and synthetic lattices. However, hot-melt adhesive formulations are modified sometimes with extenders which have the dual effect of providing both cost reduction and tackifying functions. Solvent adhesive formulas often can be manipulated through varying the solids and viscosity ratio to provide sufficient wet tack without the need for tackifier addition.

Tackifiers are included in adhesive formulations to increase the adhesion of the polymer to various substrates. This is accomplished by facilitating the wetting of the substrate by reducing the viscosity of the hot-melt. Tackifiers tend to be grouped into three general categories: hydrocarbon resins (such as aliphatic olefin and diolefins, styrene, alkyl benzene, vinyl toluene and indene), rosin esters (such as gum rosin, wood rosins and tall oil rosin) and polyterpenes (such as alpha-pinene, beta-pinene and dipentene). Common tackifiers include rosin derivatives, coumarone-indene resins, terpene oligomers, aliphatic petroleum resins and alkyl modified phenolics.

Waxes are included in hot-melt adhesive-based ink formulations for several reasons, two of which are to lower cost and to reduce viscosity. Properties affected by the wax content are blocking characteristics, softening point, and open time. High melting microcrystalline waxes, synthetic waxes and higher melting paraffin waxes are used extensively in hot-melt adhesive formulations.

Many of the adhesive binders of the adhesive-based inks of the present invention, especially hot-melt, exhibit a potential for oxidation reactions. The oxidation of adhesive bases, either through the aging process or through the effects of the application heat can seriously impair their performance. A list of common antioxidants is given in McCutcheon's Functional Materials (1991), pgs. 13–18. Typical compounds include: CAO® from PMC Specialties Group, Inc. of Cincinnati, Ohio; Cyanox® from American Cyanamid Co. of Wayne, N.J.; Good-rite® from the B. F. Goodrich Co. of Cleveland, Ohio; Irganox® from Ciba-Geigy Corp. of Hawthorne, N.Y.; Octolite from Tiarco Chemical Division of Dalton, Ga. and Tenox® from Eastman Chemical Products, Inc. of Kingsport, Tenn.

Having described the various additives which can be used in conjunction with the adhesive-based inks of the present invention, the relative amounts of certain of the additives should be taken into account in formulating the adhesive-based inks. Ethylene vinyl acetate, as shown by the testing below, works very well as a binder for the adhesive-based inks of the present invention. A typical ethylene vinyl acetate-based hot-melt is composed mainly of three components: (1) a polymer, 30–40%; (2) a tackifier, 30–40%, and (3) a petroleum wax 20–30%. The quantity and relative amount of each material is governed by the performance requirements of the adhesive. The hot-melt binder and the pigment/dye are mixed while the binder is in the molten state. The pigment concentrates usually are supplied using the binder polymer as the base material. For water-based or solvent-based adhesives, the pigment/dye concentrates are mixed directly into the adhesives and stirred well to assure a dispersion of the pigment/dye in the adhesive media.

The adhesive-based inks once formulated, must have viscosities which are compatible with the particular type of ink printing equipment and process being utilized as described in further detail below. Generally speaking, with water-based and solvent-based, adhesive-based inks the solution viscosity will range between about 50 and about 5000 centipoise, whereas for hot-melt adhesive inks the melt viscosity will range between about 100 and about 50,000 centipoise. With certain types of equipment, the viscosities may have to be adjusted up or down so that uniform applications with sufficient print quality can be achieved. Usually this can be adjusted by increasing or decreasing the amount of water or solvent and/or adding more thickening agent or low molecular weight compounds to the adhesive-based ink.

Depending upon the particular process and equipment being used to print the polyolefin-based substrate, the adhesive-based ink can be applied directly to the polyolefin-based substrate or the ink can be transferred to a transfer surface such as a printing roll and then from the transfer surface to the actual polyolefin-based substrate. Generally speaking, the adhesive-based inks and polyolefin-based substrates of the present invention are suitable for use with rotogravure, flexographic, screen printing and ink jet printing equipment. With rotogravure, flexographic and screen printing equipment, the adhesive-based ink is transferred to a printing transfer surface which contains the actual printed patterns and then from the transfer surface the ink is transferred directly to the polyolefin-based substrate. In contrast, with ink jet printing, the ink is sprayed directly onto the polyolefin-based substrate without the use of an intermediate transfer surface. Depending upon the particular type of adhesive-based ink being used and the particular end use, one type of equipment may pose advantages or disadvantages as compared to another type of equipment. For example, when multiple colors are needed, flexographic printing is usually more desirable due to its ability to handle multiple colors. With flexographic printing equipment it is also easier to change the graphics and the printing plates are less expensive than some of the other equipment. It should be noted, however, that flexographic printing equipment is currently limited to water and solvent-based, adhesive inks. Furthermore, care should be taken when using certain solvent-based inks as they may interfere or react with the rubber on the printing rolls thereby compromising the quality of the printing process and possibly damaging the equipment. In comparison, screen printing equipment is relatively costly and only one color can be used per screen. Screen printing is used primarily for water-based and hot-melt, adhesive-based inks and it should be noted that the equipment cannot be run as fast as, for example, flexographic printing equipment. Typically when using hot-melt, adhesive-based inks in conjunction with this equipment, the temperature range for the inks will be between about 140° F. and about 300° F.

If single color, high quality printing is desired, rotogravure printing is perhaps the best process with respect to the present invention. Rotogravure printing uses a print roll which is engraved therefore greatly increasing the life of the print pattern. Due to the engraving of the roll, it is also possible to get higher definition with respect to the printed pattern or graphics imparted to the polyolefin-based substrate. Furthermore, rotogravure equipment generally can be run at a higher speed than most of the other equipment and is suitable for use with water-based, solvent-based and hot-melt, adhesive-based inks according to the present invention.

Ink jet printing equipment generally requires inks that have a very low viscosity, often in the range of 1 to 10 centipoise in order to achieve appropriate processing and application. Water-based, adhesive-based inks such as polyvinyl alcohol can be brought into this range and, furthermore, water-based and solvent-based, adhesive-based inks can be used in combination with the ink jet printing equipment. An additional advantage of ink jet printing equipment is the relatively high speed at which it can be run. However, only one color can be used per jet but multiple jets can be used.

Yet another way to apply the adhesive-based inks to the polyolefin substrates of the present invention is through the use of extrusion coating equipment. Extrusion coating equipment can be used to apply much wider and usually thicker coatings of adhesive-based inks to the surface of polyolefin-based substrates such as nonwovens. Such equipment and application techniques may be suitable where large areas of colored ink need to be applied. In turn, once these large areas of ink have been applied, it is possible to print other inks over top of the extrusion-coated layer.

Once the adhesive-based ink has been applied to the polyolefin-based substrate, the substrate can then be wound up on a wind up roll or the printed substrate can continue in line for further processing. In either event a certain amount of time will be needed to allow the adhesive-based ink to dry on the polyolefin-based substrate. As a result, conventional heating equipment can be employed in line to hasten the drying of the adhesive-based ink.

Having described the materials and equipment suitable for use with the present invention, a series of inks were prepared and then printed onto a polyolefin-based substrate, in this case a spunbond polypropylene web. The dry crock test method was used to measure whether these combinations of adhesive-based inks and polyolefin-based nonwovens had sufficient abrasion resistance. The dry crock test method was based upon American Association of Textile Chemists and Colorists (AAPCC) Test Method 116–1983 which is incorporated herein in its entirety with two modifications. The test method consisted of essentially rubbing a 2"×2" square cotton test swatch against the (dry) material of interest for a specific number of turns while maintaining a constant pressure supplied by a standard weight (40 ounces). According to the test procedure, the test swatches were then analyzed using a Hunter Colorimeter for the CIELAB color difference which is expressed as $\Delta E$. The $\Delta E$ was then converted to a number between 1 and 5 using the following equation: C.R.=A exp. (−B) where A=5.063244 and B=0.059532 ($\Delta E$) if $\Delta E$ is less than 12 or A=4.0561216 and B=0.041218 ($\Delta E$) if $\Delta E$ is greater than 12. This number C.R. is the crock value. A crock value of 1 corresponds to a low or bad result while a value of 5 is the highest possible test result and this value would indicate that essentially no color was rubbed off the sample material.

AATCC Test Method 116-1983 as summarized above was modified in the following manner. In the official test, a 20 turn rubbing procedure is standard, however, under the modified test method used herein, a 5 turn rubbing procedure was used. The 5 turns were used because the test substrates of the present invention cannot generally endure the severe abrasion incurred during a 20 rub procedure given the 40 ounce loading as indicated by the fibers roping and/or holes appearing in the material when nonwoven webs are being tested. Thus the 5 turn rubbing procedure represented a more reasonable abrasion of the materials during usage as would typically be encountered if a printed, polyolefin-based nonwoven web was used as a medical fabric or an outercover on a personal care product such as a diaper or training pant. The second change in the test for use with the present invention was that the amount of color transferred to the test swatch was measured using a Hunter Colorimeter instead of the AATCC Chromatic Transference Scale or grade scale measuring device. With the colorimeter, greater objectivity in evaluating the results was possible due to less operator dependence and it was also possible to achieve higher efficiency and consistency for on-line quality assurance. The Hunter Colorimeter was Model D25 manufactured by Hunter Associates Laboratory, Inc. of Reston, Va. The crock test was performed using AATCC crock meter Model CM-6 supplied by Atlas Electric Device Company of Chicago, Ill. and the Cielab $\Delta E$ value was determined using a Hunterlab Model D25 Optical Sensor manufactured by Hunter Associates Laboratory, Inc. of Reston, Va.

In order to demonstrate the durability of the materials according to the present invention, a series of samples were generated in accordance with the foregoing description of the materials and processes. A total of nineteen samples were prepared using standard store bought fabrics, various polyolefin-based substrates and various inks including what would be referred to as standard "off-the-shelf inks" in addition to adhesive-based inks according to the present invention.

SAMPLES 1 AND 2

The first two samples were printed woven fabrics purchased off-the-shelf from a fabric store. Sample 1 was simply a woven cotton material and sample 2 was a woven polyester material. Both commercial fabrics were already printed with colored patterns using normal fabric dyes. No additional printing was done to the fabrics. A two inch by two inch sample of each material was subjected to the crock test as described above. Sample 1, the cotton sample, had a crock value or rating of 4.5 on a scale of 1 to 5 as shown in Table 1 below. Sample 2, the polyester sample, had a crock rating of 4.6. Thus, both of these samples confirmed the fact that it is possible to print common fabrics and get good abrasion resistance. See Table I.

SAMPLES 3 THROUGH 5

With samples 3 through 5, the substrate was a polypropylene spunbond (PP SB) nonwoven web and the ink was a solvent-based Multibond® ink manufactured by the Sun Chemical Corp. of Fort Lee, N.J. The polypropylene web had a basis weight of one ounce per square yard and was manufactured by the assignee of record, Kimberly-Clark Corporation of Neenah, Wis., utilizing approximately 3.5 denier fibers thermally bonded to one another with an overall bond area of fifteen percent. An example of how to make such a material can be found in U.S. Pat. No. 4,340,563 to Appel et al. which is incorporated herein by reference in its entirety. The ink was applied to each of the webs using flexographic printing equipment running at 400 feet per minute and, again, two inch by two inch samples were measured for abrasion resistance. As can be seen in Table 1, the samples respectively had crock ratings of 2.5, 2.9 and 2.7 for and average of 2.7. At this crock value the materials exhibited poor abrasion resistance thereby demonstrating the poor adhesion of normal inks to nonpolar materials such as polyolefins. See Table I.

SAMPLES 6 THROUGH 8

With samples 6 through 8 the same polypropylene spunbond substrate was used as with samples 3 through 5. The difference between these and the preceding samples was the type of ink that was applied to the nonwoven web. With sample 6 the adhesive-based ink used an ethylene vinyl acetate (EVA) binder with a conventional pigment in a binder to pigment ratio in the range of approximately 10:1 to 8:1. The pigmented EVA-based adhesive ink was supplied by Findley Adhesives, Inc. of Wauwatosa, Wis. and the EVA bore the code L-8173E. The adhesive was water-based, contained a defoaming agent and had a solids content of approximately 50%. The adhesive ink was printed on the polypropylene spunbond web using flexographic printing equipment running at approximately 400 feet per minute. A sample of the printed material was analyzed for abrasion resistance and was found to have a crock value of 4.4, a value comparable to the standard cotton and polyester fabrics printed with normal inks. This too represented a significant increase in abrasion resistance over the same polyolefin substrates printed with a normal ink as with samples 3 through 5.

With sample 7 the substrate was the same as with samples 3 through 6, the difference again being the type of adhesive-based ink used. In this case the binder was water-based polyvinyl alcohol and included a conventional pigment. The binder to pigment ratio was approximately 12:1 to 8:1. This particular version of a water-based, adhesive ink was manufactured by the same company as the EVA in example 6. The adhesive-based ink was applied to the polypropylene substrate using flexographic type printing equipment and a two inch by two inch sample was tested for abrasion resistance. Once again the sample had a high crock rating (4.3) thereby demonstrating the superior adhesion of the combination.

With sample 8 the same type of polypropylene spunbond web was treated with a polyurethane-based, solvent-based adhesive. The polyurethane was identified as Eccobrite™ Clear Base EB 411-31A from Eastern Color and Chemical Company of Providence, R.I. To the adhesive there was added an orange pigment labeled R7339 which was also supplied by the Eastern Color and Chemical Company. The binder to pigment ratio was between approximately 10:1 and 8:1 and the ink was applied using flexographic printing equipment. After the ink had been applied to the substrate it was allowed to dry using moderate heating and a two inch by two inch sample was cut and tested for abrasion resistance. The sample had a crock rating of 4.6 which once again illustrated the excellent adhesion between the polyolefin-based substrate and the adhesive-based ink. See Table I.

TABLE I

| Sample # | Fabric | Ink | Crock Rating |
|---|---|---|---|
| 1 | printed cotton woven | No additional ink | 4.5 |
| 2 | printed PET woven | No additional ink | 4.6 |
| 3 | PP SB | regular ink | 2.5 |
| 4 | PP SB | regular ink | 2.9 |
| 5 | PP SB | regular ink | 2.7 |

TABLE I-continued

| Sample # | Fabric | Ink | Crock Rating |
|---|---|---|---|
| 6 | PP SB | EVA | 4.4 |
| 7 | PP SB | polyvinyl alcohol | 4.3 |
| 8 | PP SB | polyurethane | 4.6 |

As mentioned previously, it is also possible to print such adhesive-based inks on polyolefin nonwoven laminates and still achieve good crockfastness. With samples 9 through 19 the polyolefin-based substrate was a polypropylene spunbond/meltblown/spunbond laminate with each layer having a basis weight of 0.35 ounces per square yard for a total basis weight of 1.05 ounces per square yard. One method for producing such a laminate is set forth in U.S. Pat. No. 4,041,203 to Brock et al. which is commonly assigned to the assignee of record, Kimberly-Clark Corporation of Neenah, Wis., and is incorporated herein by reference in its entirety.

As shown in Table II below, six inks were separately applied to samples of the polypropylene nonwoven web and then tested for colorfastness using the crock rating. Sample 9 used a regular, non-adhesive-based ink, Aqua brite reflex blue (AB-2504) supplied by B&B Ink and Laquer, Inc. of Atlanta, Ga. Samples 10 through 19 all used adhesive-based inks. Samples 10–12 used a water-based EVA latex (Airflex® 401) from Air Products and Chemicals, Inc. of Allentown, Pa.

Samples 13 through 15 used a water-based polyvinyl alcohol (Airvol® 203) with a hydrolysis of between 87 and 89 percent from Air Products and Chemicals, Inc. Samples 16 through 18 used another water-based EVA latex (DUR-O-SET® E-623) from National Starch and Chemical Company of Bridgewater, N.J.

Sample 19 used another water-based polyvinyl alcohol (Airvol® 125) as the binder with a hydrolysis in excess of 99.3 percent. Airvol® 125 is a product of Air Products and Chemicals, Inc. To color the adhesive-based inks of samples 10 through 19, a pigment was added to each of the samples in a binder to pigment ratio shown in Table II. The pigment was a copper phthalocyanine blue pigment (MONOLITE® Blue BXE-HD) from ICI Americas, Inc. of Wilmington, Del. Binder to pigment ratios ranged between 90:10 to 60:40 on a dry weight basis. In each case the ink (sample 9) or adhesive-based ink (samples 10 through 19) was printed onto one side of the polypropylene spunbond/meltblown/spunbond laminate using flexographic printing equipment.

As can be seen from Table II below, sample 9 which used an ordinary ink had very poor adhesion to the polyolefin substrate thereby yielding poor colorfastness as indicated by a crock value of 1.5. In contrast, the samples which used an adhesive-based ink in conjunction with a polyolefin-based substrate (samples 10 through 19) showed excellent colorfastness with crock ratings from 4.0 (sample 12) to as high as 4.7 (samples 10, 13 and 19).

TABLE II

| Sample | Adhesive | Binder/Pigment | Colorfastness |
|---|---|---|---|
| 9 | regular ink | N/A | 1.5 |
| 10 | Airflex 401 | 90/10 | 4.7 |
| 11 | " | 80/20 | 4.3 |
| 12 | " | 70/30 | 4.0 |
| 13 | Airvol 203 | 80/20 | 4.7 |

TABLE II-continued

| Sample | Adhesive | Binder/Pigment | Colorfastness |
|---|---|---|---|
| 14 | " | 70/30 | 4.6 |
| 15 | " | 60/40 | 4.4 |
| 16 | Dur-o-set | 90/10 | 4.4 |
| 17 | E-623 | 80/20 | 4.2 |
| 18 | " | 70/30 | 4.2 |
| 19 | Airvol 125 | 80/20 | 4.7 |

SAMPLE 20

In sample 20 a three layer nonwoven laminate was printed with a solvent-based adhesive ink. The nonwoven was a spunbond/meltblown/spunbond composite having a basis weight of 1 ounce per square yard. The nonwoven was manufactured according to the teachings of U.S. Pat. No. 4,041,203 to Brock et al. Printed on one side of the nonwoven was an adhesive-based ink produced by the National Starch and Chemical Company of Bridgewater, N.J. and labeled Spraymaster® 81-0388. The adhesive-based ink had a solvent base and continued neoprene rubber and red pigment. Printing was via a flexographic hand proofer supplied by Panarco Company of Summit, N.J. This type of equipment closely simulates the action of a commercial flexographic printing press. Once a sample had been prepared, a 2 inch by 2 inch piece was cut and tested for colorfastness using the crock test described above. The sample had a crock value of 4.8.

Materials such as those in samples 10 through 19 can and have been converted into outercovers for personal care products such as diapers, training pants, sanitary napkins, incontinence garments and bandages. Typically these products have a liquid pervious top sheet or liner which is placed adjacent the wearer's skin. On the outside of the product there is a backing sheet which, in most instances, is substantially liquid impervious to prevent leakage of the retained liquid such as urine, feces, menses and blood. This backing sheet may or may not be breathable. To absorb such liquids there is usually an absorbent core disposed between the top sheet and backing sheet. Such absorbent cores are usually made from natural or synthetic wood pulp and can include superabsorbents, hydrogels or hydrocoloids to enhance the fluid retention properties of the product. The adhesive-based ink coated polyolefin substrates of the present invention can be used for both the top sheet and the backing sheet of the personal care product. When used as a backing sheet, it is usually desirable to place a totally liquid-impervious material, such as a film, between the polyolefin nonwoven and the absorbent core, to control leakage. The backing sheet of training pants is one area which is particularly well-suited for use of the present material due to the high level of abrasion which can be encountered by such training pants.

Having thus described the invention in detail, it should be appreciated that various modifications and changes can be made in the present invention without departing from the spirit and scope of the following claims.

We claim:

1. A personal care absorbent article comprising a liquid pervious top sheet and a substantially liquid impervious backing sheet with an absorbent core disposed between said top sheet and said backing sheet, said backing sheet including a nonwoven web comprising a plurality of polyolefin fibers thermally bonded to one another and an adhesive-based ink printed on at least one surface of said nonwoven web to form an adhesive-based ink-printed nonwoven web, said adhesive-based ink including a ethylene vinyl acetate binder having a viscosity of between about 50 and 10,000 cps during application, and a pigment with a binder to pigment ratio of between about 10:1 and 1:1 on a dry weight basis of the total solids content in said adhesive-based ink, said adhesive-based ink-printed nonwoven web having a crock value of at least 4.

2. The personal care absorbent article of claim 1 wherein said article is a training pant.

3. The personal care absorbent article of claim 1 wherein said article is a diaper.

4. The personal care absorbent article of claim 1 wherein said article is an incontinence garment.

5. The personal care absorbent article of claim 1 wherein said article is a sanitary napkin.

* * * * *

UNITED STATES PATENT AND TRADEMARK OFFICE
CERTIFICATE OF CORRECTION

PATENT NO. : 5,695,855

DATED : December 9, 1997

INVENTOR(S) : Richard Swee-Chye et al.

It is certified that error appears in the above-identified patent and that said Letters Patent is hereby corrected as shown below:

Column 1, Item 75, "Swee-chye" should read
--Swee-Chye--;
Column 3, line 45, "consumer--training" should read
--consumer-training--;
Column 3, line 53, "is" should read
--has--;
Column 5, line 7, "as well straight" should read"
--as well as straight--;
Column 6, line 55, "390and" should read
--390 and--;
Column 6, line 64, "an" should read
--a--;
Column 8, line 60, "dupont" should read
--duPont--;
Column 13, line 2, "and" should read
--an--;
Column 14, lines 22-36, should be one paragraph;
Column 14, line 42, "THe" should read
--The--.

Signed and Sealed this

Thirtieth Day of March, 1999

Attest:

Q. TODD DICKINSON

Attesting Officer

Acting Commissioner of Patents and Trademarks